United States Patent

Brown

[11] Patent Number: 5,431,634
[45] Date of Patent: Jul. 11, 1995

[54] AMBULATORY PUMP

[75] Inventor: Jeffrey O. Brown, Logan, Utah

[73] Assignee: Baxter International Inc., Deerfield, Ill.

[21] Appl. No.: 83,927

[22] Filed: Jun. 28, 1993

Related U.S. Application Data

[63] Continuation-in-part of Ser. No. 847,523, Mar. 6, 1992, abandoned.

[51] Int. Cl.⁶ .................. A61M 1/00; F04B 17/00
[52] U.S. Cl. .................... 604/153; 604/131; 417/479; 417/413.1
[58] Field of Search .............. 604/131, 132, 134, 151, 604/141, 153, 152, 892.1; 222/214, 209, 212, 207; 417/479, 480, 412, 413

[56] References Cited

U.S. PATENT DOCUMENTS

| | | |
|---|---|---|
| 4,152,098 | 5/1979 | Moody et al. |
| 4,336,800 | 6/1982 | Giovanni |
| 4,411,603 | 10/1983 | Kell |
| 4,453,931 | 6/1984 | Pastrone |
| 4,453,932 | 6/1984 | Pastrone |
| 4,519,792 | 5/1985 | Dawe |
| 4,557,725 | 12/1985 | Heyne et al. |
| 4,594,058 | 6/1986 | Fischell |
| 4,898,585 | 2/1990 | Borsanyi et al. ............ 604/153 |
| 4,927,411 | 5/1990 | Pastrone et al. |
| 4,995,864 | 2/1991 | Bartholomew ............ 604/153 |
| 5,017,100 | 5/1991 | Arkans ............ 417/413 R |
| 5,053,031 | 10/1991 | Borsanyi ............ 604/153 |
| 5,152,753 | 10/1992 | Laguett et al. ............ 604/153 |
| 5,176,510 | 1/1993 | Nilsson ............ 417/479 |

Primary Examiner—John G. Weiss
Attorney, Agent, or Firm—Paul E. Schaafsma; Paul C. Flattery

[57] ABSTRACT

A pump 10 for delivering a precise selected output volume has a rigid pump housing 12. A diaphragm 16 is in fluid right abutment with the pump housing 12 to define a pump chamber 40 therebetween. The diaphragm 16 is resiliently biased towed a selected metering position 46 wherein the diaphragm 16 assumes a cup-shaped configuration and the pump chamber 40 has a selected metering volume. The diaphragm 16 is drivable to a discharged position 52 wherein the pump chamber 40 has a selected discharge volume less than the metering volume by a selected output volume. The diaphragm 16 maintains the output volume substantially constant notwithstanding substantial variations in fluid pressure from the fluid supply of variations in ambient pressure. An inlet 32 selectively allows fluid to flow between a fluid supply 45 and the pump chamber 40 as the diaphragm 16 moves from the discharged position 52 to the metering position 46. The inlet 32 stops the fluid flow between the pump chamber 40 and the diaphragm 16 when the diaphragm 16 is driven from the metering position 46. A one-way outlet valve 28 in fluid communication with the pump chamber 40 permits flow of the output volume out of the pump chamber 40.

22 Claims, 3 Drawing Sheets

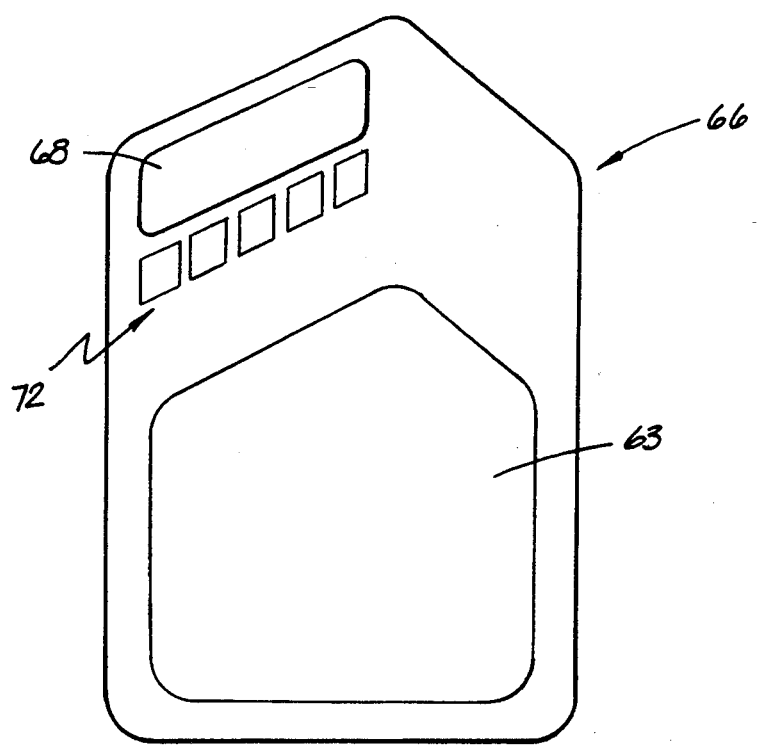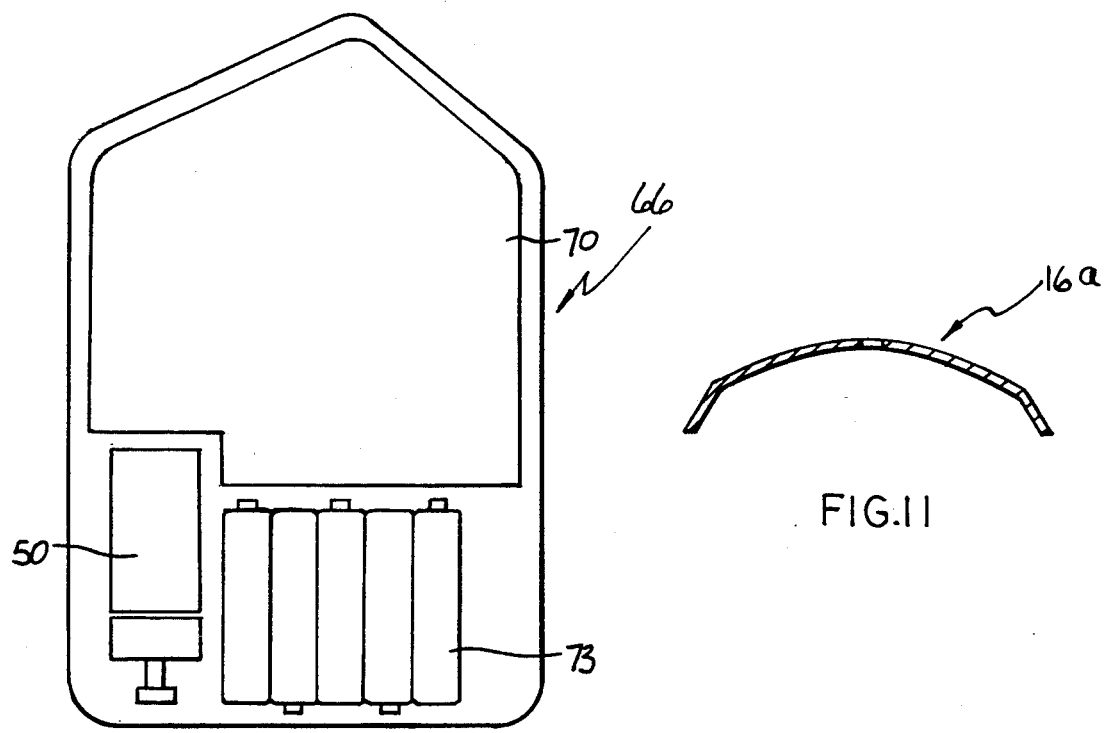

AMBULATORY PUMP

This application is a continuation-in-part of U.S. patent application Ser. No. 847,523, filed Mar. 6, 1992, now abandoned.

BACKGROUND OF THE INVENTION

Technical Field

The present invention is directed toward a pump for providing a precise selected output volume and, more particularly, toward an ambulatory infusion pump insertable into a control unit having a cyclical or reciprocating drive for delivering a precise selected output volume of fluids for intravenous or intra-arterial injection into a patient.

Background Art

Use of infusion pumping devices for parenternal delivery of fluid to patients in hospitals or other patient care locations has increased dramatically in recent years. Infusion pumps have replaced gravity control infusion systems in some applications because of their greater accuracy in delivery rates and dosages and their ability to permit varying medication delivery profiles to optimize medication effectiveness. Infusion pumps have been particularly useful for delivering dangerous drugs to patients over an extended period of time in precisely measured and timed volumes to maximize drug effectiveness and patient safety.

In recent years, spiraling hospital costs and shortages of critical facilities have led to efforts to allow earlier dismissal of patients from hospitals. As a result, numerous ambulatory infusion pumps have been developed. These ambulatory infusion pumps, like the stationary infusion pumps which preceded them, require a great degree of accuracy in the administration of fluids to maximize the effectiveness of medication and to protect the patient. Typically, these ambulatory infusion pumps include a pump control unit and drive mechanism including a variety of operating controls adapted to accept a disposable pump cassette containing the pump mechanism. The control unit and pump cassette must be small and light enough to be readily carried by patients. The pump cassettes are preferably disposable to reduce the risk of spreading disease when the control units are reused and to prevent the inadvertent mixing of drugs. As a result, they must be relatively small and economically manufactured to minimize costs and encourage their use. Notwithstanding, the accuracy of their output volumes must be precisely maintained.

Ideally, infusion pumps exhibit monotonicity, a high degree of pump linearity and a high degree of variability in selection of pump granularity. Monotonicity means that an incremental physical displacement will yield an incremental volume displacement. Pump linearity is a measure of the pump's ability to apply substantially identical incremental volume displacements for each cycle. Finally, granularity is a measure of the size of each incremental volume displacement comprising a desired total volume displacement. The ideal pump exhibits these characteristics while requiring a minimum amount of power, weight and size.

In an effort to meet these requirements, the prior art has looked to different types of pumps. For example, rotary peristaltic pumps have been used, but such pumps are neither monotonic nor linear. Linear peristaltic pumps also have inadequate linearity. Syringe pumps have been complicated mechanisms which are expensive to construct and bulky. Thus, syringe pumps are not ideal for an ambulatory infusion pump.

Positive displacement pumps have also been used having an elastomeric diaphragm actuated by a solenoid controlled armature. The diaphragm acts like a piston to increase or decrease the size of a pump chamber defined by a rigid pump housing. As the volume of the pump chamber moves from its minimum to its maximum, medication is drawn into the chamber from a reservoir through a one-way input valve. As the armature drives the diaphragm into the chamber, thus decreasing the volume of the chamber, fluid is driven out of the chamber through a one-way output valve. In many of these structures, however, the diaphragm is subject to deformation due to variations in reservoir pressure or ambient pressure. As a result, the output volume is subject to variation, creating a serious problem where potentially dangerous drugs are being administered. Moreover, the valving systems of these pumps are typically spring biased, making them relatively complicated and expensive to build.

One way to overcome the variation in output volume these pumps can exhibit is shown in Fischell, U.S. Pat. No. 4,594,058. Fischell uses a structure similar to the above-described prior art, only provides a rigid housing which contorts the flexible elastomeric diaphragm in an effort to deliver a more precise, constant stroke volume independent of ambient and reservoir pressures. However, this structure is relatively bulky, complicated and expensive to build.

SUMMARY OF THE INVENTION

The present invention is directed toward overcoming one or more of the problems discussed above.

A pump for delivering a selected output volume of fluid from a fluid supply to an output conduit in response to driving by a cyclical or reciprocating drive has a rigid pump housing. A diaphragm is in fluid tight abutment with the pump housing to define a pump chamber therebetween. The diaphragm is resiliently biased toward a selected metering position in which the diaphragm assumes a cup-shaped configuration and the pump chamber has a selected metering volume. The diaphragm is drivable by the cyclical drive to a discharged position in which the pump chamber has a selected discharged volume which is less than the metering volume by a selected output volume. The diaphragm maintains the output volume substantially constant notwithstanding substantial variations in fluid pressure from the fluid supply or variations in ambient pressure. An inlet selectively allows fluid to flow between the fluid supply and the pump chamber as the diaphragm moves from the discharged position to the metering position. The inlet stops the fluid flow between the pump chamber and the fluid supply when the diaphragm is driven from the metering position. A one-way outlet valve in fluid communication with the pump chamber permits the flow of the output volume out of the pump chamber.

The inlet preferably consists of an inlet hole defined by the diaphragm. A relaxation seal is resiliently biased away from the inlet hole, the relaxation seal closing the inlet hole in response to the cyclical drive driving the diaphragm from the metering position. The diaphragm is preferably a convex dome of spring steel with the inlet hole in the center of the convex dome. The output volume will remain constant notwithstanding variations of atmosphere or reservoir pressure within a range of 7-30 psia (pounds per square inch absolute).

Another aspect of the present invention is a pump having a rigid housing with a diaphragm having a peripheral edge secured to the housing about the peripheral edge to define a pump chamber therebetween. The diaphragm includes an inlet opening from the pump chamber to a fluid supply. The diaphragm is resiliently biased toward a metering position within the chamber having a first selected volume. The diaphragm is drivable in response to the cyclical drive from the metering position to a discharged position having a second selected volume which is less than the first selected volume by a selected output volume. The cyclical drive engages the diaphragm inlet during driving to close the diaphragm inlet when the diaphragm is driven from the metering position by the cyclical drive. A one-way outlet valve in fluid communication with the pump chamber permits flow of the output volume of fluid out of the pump chamber.

Preferably, the diaphragm is a convex dome of spring steel with the inlet in the center of the dome and the cyclical drive engaging the center of the dome during driving. The closure is preferably a relaxation seal resiliently biased from the diaphragm inlet, the relaxation seal closing the diaphragm inlet in response to the cyclical drive when driving the diaphragm from the metering position.

Yet another aspect of the present invention is a disposable ambulatory infusion pump cassette usable with a control unit having a cyclical drive to deliver a selected output volume of fluid to an output conduit for parenteral injection of selected output volume to a patient. The cassette includes the above-described pump with the diaphragm disposed within a reservoir bag.

The ambulatory infusion pump of the present invention delivers a precise output volume in response to actuation by a cyclical drive. The diaphragm of the pump is not subject to deformation by changes in ambient or reservoir pressures within a range of about 7-30 psia. The diaphragm is also biased toward a select metering position and, as the diaphragm is deformed by a cyclical pump, it is biased toward a select discharged position. Thus, monotonicity and linearity are assured. Moreover, the output volume of the pump structure can be varied by altering the size of the diaphragm. Thus, a high degree of variability in selection of pump granularity can be achieved with the inventive pump structure. The ambulatory pump of the present invention has relatively few pieces, making it easy and inexpensive to assemble. Moreover, the elements of the ambulatory pump are simple and inexpensive to manufacture, further decreasing the cost of the pump. In addition, the elements are relatively lightweight and compact. In summary, the ambulatory infusion pump of the present invention delivers a precise output volume, is lightweight, compact and inexpensive, making it ideal for incorporation into a disposable reservoir/pump cassette for use with a cyclical drive control unit.

BRIEF DESCRIPTION OF THE DRAWINGS

FIG. 9 is a top plan view of an ambulatory pump control unit for use with the ambulatory pump;

FIG. 10 is a top plan view of a control unit for use with the ambulatory pump of the present invention with a cover piece removed; and FIG. 11 is an alternate embodiment of the diaphragm of the ambulatory pump of the present invention.

DETAILED DESCRIPTION OF THE PREFERRED EMBODIMENT

Figure 1:
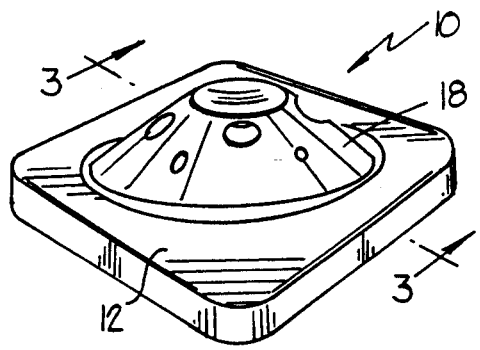
FIG. 1 is a perspective view of the ambulatory pump of the present invention.
Figure 2:
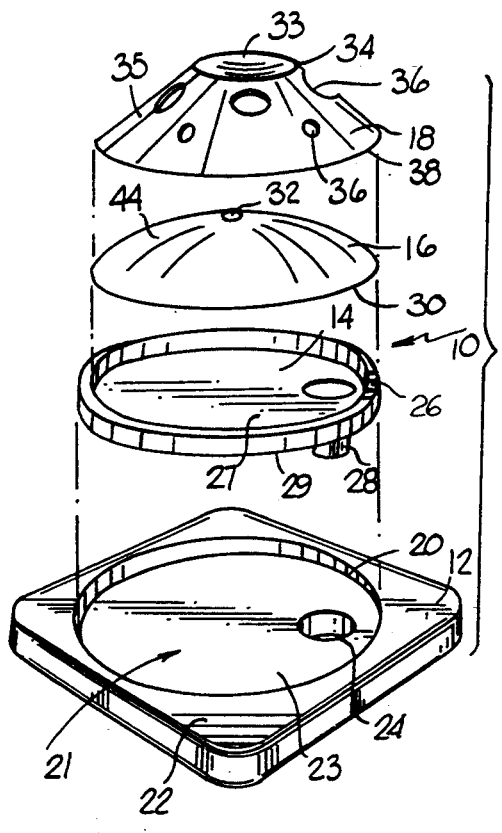
FIG. 2 is an exploded perspective view of the ambulatory pump of the present invention.

An ambulatory infusion pump 10 of the present invention is illustrated in FIG. 1. As seen in FIG. 2, the ambulatory infusion pump 10 includes a rigid housing 12, a fluid seal 14, a dome or diaphragm 16 and a relaxation seal 18.

The rigid housing 12 has an annular shoulder 20 defining a cylindrical depression 21 in its top surface 22. At the bottom 23 of the cylindrical depression 21 is a cylindrical outlet bore 24 through a stepped nozzle 25 (see FIGS. 3-5) extending downward from the rigid housing 12.

The fluid seal 14 has an annular ridge 26 extending upward from its top surface 27. A one-way seal or duckbill 28 extends downward from the bottom surface 29 of the fluid seal 14 to allow one-way fluid communication between top surface 27 of the fluid seal 14 and the exterior of the pump 10. The one-way valve 28 is configured to be received in the outlet bore 24 of the rigid housing 12, as illustrated in FIGS. 3-5 and 7-8. The fluid seal 14 is of a circular configuration and of a diameter such that when the diaphragm 16 is mated inside the annular ridge 26 of the fluid seal 14. The fluid seal 14 and diaphragm 16 are held within the cylindrical depression 21 of the housing 12 by a friction fit.

The diaphragm 16 is a convex dome (i.e., cup-shaped) and has a peripheral edge 30 configured so that, when the ambulatory pump is assembled as illustrated in FIGS. 3-5 and 7-8, the peripheral edge 30 abuts the fluid seal 14 and is radially confined by the annular shoulder 20 of the rigid housing 12. An opening or inlet 32 is disposed in the center of the diaphragm 16.

The relaxation seal 18 is generally cup-shaped with a concave plug 33 at its top 34 and a biasing support side wall 35 for resiliently biasing the concave plug 33 upward away from the diaphragm inlet 32. A plurality of perforations 36 are in the side wall 35 of the relaxation seal 18. The periphery 38 of the relaxation seal 18 is configured so that the relaxation seal 18 envelops the diaphragm 16 when the ambulatory pump is in its assembled configuration as illustrated in FIGS. 3–5 and 7–8.

When assembled, the fluid seal 14 fits in the cylindrical depression 21 of the housing 12 with the one-way seal 28 received in the outlet bore 24 of the housing 12. The diaphragm 16 in turn fits in the fluid seal 14 and rests with its peripheral edge 30 against the seal top surface 27 and radially confined by the annular ridge 26 of the fluid sea/14 and the annular shoulder 20 of the housing 12. The relaxation seal 18 in turn is received within the fluid seal 14 to cover or envelop the diaphragm 16 with the seal peripheral edge 38 of the relaxation seal 18 also radially confined by the annular ridge 26 of the fluid seal 14 and the annular shoulder 20 of the housing 12. A friction fit or clips, adhesives, fasteners and the like (not shown) maintain the assembled components of the pump 10 in their assembled configuration.

Figure 3:
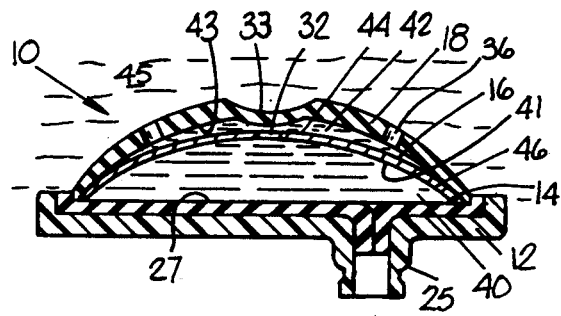
FIG. 3 is a cross-sectional view of the ambulatory pump of the present invention taken along line 3—3 of FIG. 1, showing the diaphragm in its metering position.
Figure 4:
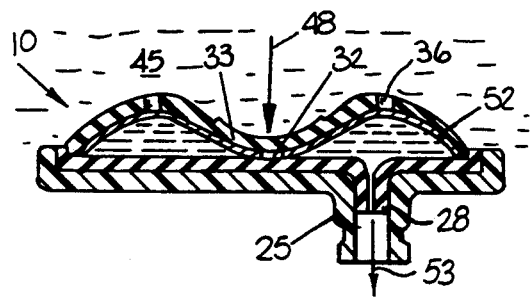
FIG. 4 is a cross-sectional view similar to FIG. 3 but showing the diaphragm in its discharged position.
Figure 5:
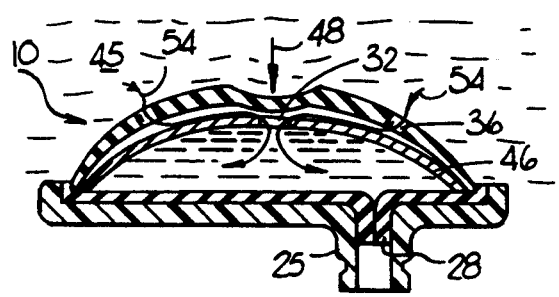
FIG. 5 is a cross-sectional view similar to FIG. 3 but showing the flow of fluid into the pump chamber as the diaphragm moves from its discharged position to its metering position.

As seen in FIGS. 3–4 and 7–8, a pump chamber or ventricle 40 is defined between the bottom 41 of the diaphragm 16 and the top surface 27 of the fluid seal 14. An atrium 42 is defined between the bottom 43 of the relaxation seal 18 and the top 44 of the diaphragm 16. Operation of the ambulatory infusion pump 10 of the present invention is best understood with reference to FIGS. 3–5. As seen in FIG. 3, the ambulatory pump 10 is shown disposed within a fluid reservoir 45. Fluid has filled the ventricle or pump chamber 40 and the atrium 42. The diaphragm 16 is resiliently biased to its point of lowest potential energy in which it has the shape of a convex dome defining a metering position 46. Similarly, the relaxation seal 18 is resiliently biased to a cup-shaped configuration With the concave plug 33 away from the inlet 32. In this configuration, a selected metering volume of fluid defined by the volume of the pump chamber 40 fills the pump chamber 40. Upon application of a drive force 48, as may be provided by a cyclical or reciprocating drive 50 (see FIG. 6), the plug 33 of the relaxation seal 18 is driven downward against the inlet 32, stopping the flow of fluid therethrough. As the diaphragm 16 is driven into its discharged position 52, illustrated in FIG. 4, fluid is forced out of the one-way valve 28 as illustrated by the arrow 53. The drive force 48 on the diaphragm 16 displaces the peripheral edge 30 of the diaphragm 16 in both a normal and a radial direction (because the diameter of the diaphragm 16 increases as it is driven towards the discharge position 52), resiliently deforming the fluid seal 14 and improving the seal between the diaphragm 16 and the fluid seal 14 as the pressure in the ventricle or pump chamber 40 increases. When the diaphragm 16 reaches the discharged position 52, an output volume of fluid has been discharged from the pump chamber 40 equal to the difference between the metering volume of the pump chamber 40 and the discharged volume of the pump chamber 40. At the discharged position 52 the diaphragm 16 is in a next to lowest state of internal potential energy, the only lower state of internal potential energy being when the diaphragm 16 is in the metering position 46. Thus, as the diaphragm 16 is urged toward the discharged position 52, the diaphragm 16 readily assumes the discharged position 52 facilitating a precise discharged position 52 and resulting output volume.

As the drive force 48 is decreased (that is, the drive 50 retracts), the diaphragm 16 is resiliently biased back to its lowest state of internal potential energy, the precise metering position 46. The fluid seal 14 in turn is resiliently biased to an undeformed configuration. Similarly, the relaxation seal 18 is resiliently biased back to its cup-shaped configuration. The one-way valve 28 closes and as the inlet 32 is opened (with the relaxation seal 18 moving clear of the inlet 32), fluid flows as indicated at 54 from the reservoir 44 through the perforations 36 in the relaxation seal 18 into the atrium 42, and from the atrium 42 through the diaphragm inlet 32 to refill the pump chamber 40 to its precise metering volume.

A diaphragm 16 in the form of a convex dome made of spring steel with an inlet 32 in the center is preferred. Provided the modulus of elasticity of the diaphragm 16 is not exceeded, the diaphragm 16 is repetitively, resiliently biased toward a precise position of lowest internal potential energy at the metering position 46, thus defining a precise metering volume, and further will repetitively assume a precise discharged position 52 of a second lowest internal potential energy when subjected to the drive force 48. Spring steel is preferred in part because, in addition to exhibiting the property of assuming a precise metering position 46 and discharged position 52 corresponding to a lowest point and second lowest point of potential energy, respectively, spring steel will assume these positions notwithstanding substantial variations in atmosphere or reservoir pressures. More particularly, variations in ambient (i.e. atmospheric) or reservoir pressures within a range of about 7–30 psia will not affect pump output, this being the anticipated range of pressures likely to be encountered in the pump's standard operating environment. Of course, still other diaphragm materials and configurations exhibiting the above required properties could be used within the scope of the invention. One such configuration is an alternate embodiment of the dome 16a shown in FIG. 11.

A cup-shaped amber surgical material or molded SILASTIC ® forms a suitable relaxation seal 18. Similarly, the fluid seal 14 is preferably made of amber surgical material or molded SILASTIC ®. The housing may be made of any suitable rigid material, such as a transparent plastic.

Figure 6:
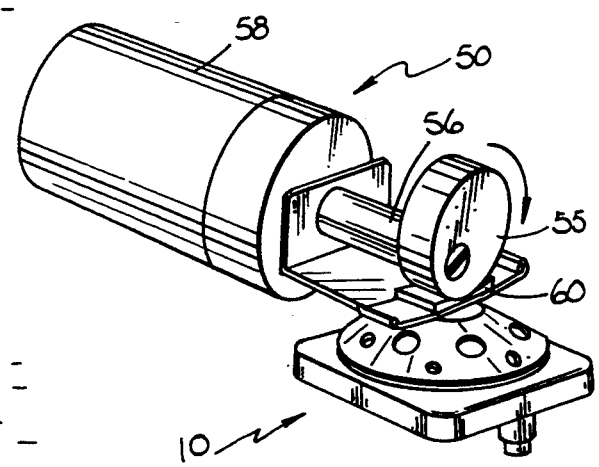
FIG. 6 is a perspective view of the ambulatory pump of the present invention with a cyclical drive operatively associated therewith.
Figure 7:
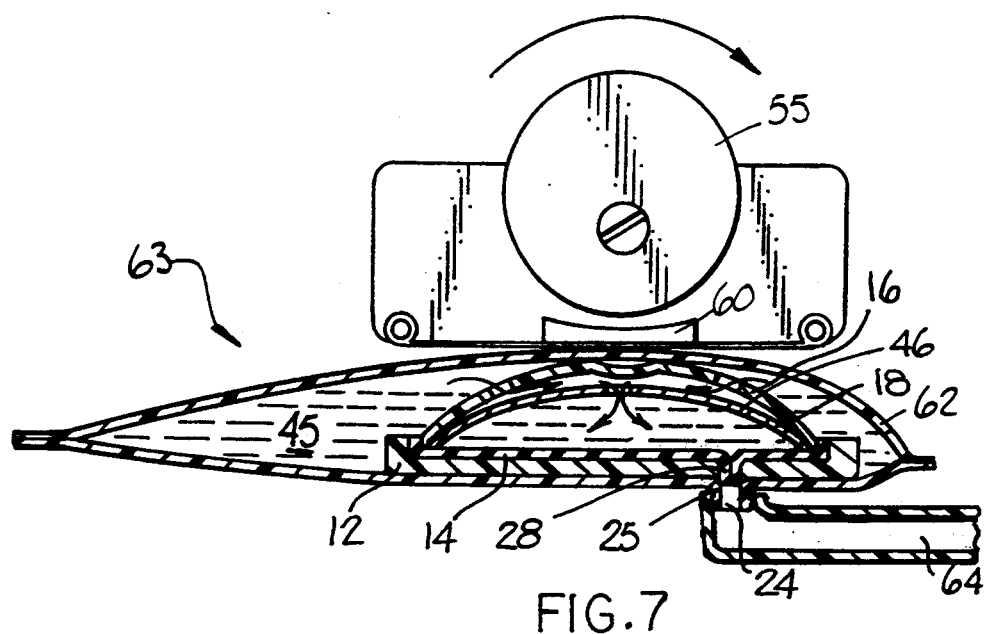
FIG. 7 is a sectional view of the ambulatory pump in combination with a reservoir bag of the present invention and further including a cyclical or reciprocating drive operatively associated therewith illustrated with the diaphragm in the metering position.
Figure 8:
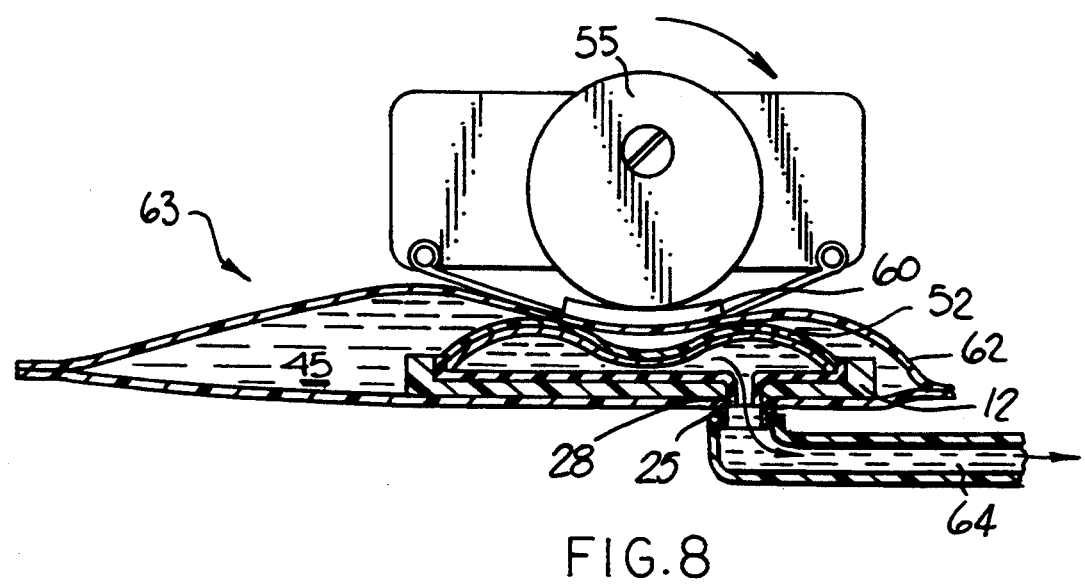
FIG. 8 is similar to FIG. 7 but with the cyclical drive having driven the diaphragm to its discharged position.

As illustrated in FIG. 6, the cylindrical drive 50 preferably includes a cam 55 connected by a drive shaft 56 to an electric motor 58. A fiction reducing beating 60 made of TEFLON ® is disposed between the cam 55 and the ambulatory infusion pump 10. FIG. 7 illustrates the ambulatory infusion pump 10 in combination with a reservoir bag 62 defining the fluid reservoir 45 to form a cassette 63. In this configuration, the fluid seal 14, the diaphragm 16 and the relaxation seal 18, as well as the rigid housing 12, are disposed within the reservoir bag 62. The beating 60 protects the reservoir bag 62 from wear caused by the cam 55. An output conduit 64 is attached to the stepped nozzle 25 in fluid communication with the output bore 24 of the housing 12. In this manner, as the diaphragm 16 is driven from the metering position 46 illustrated in FIG. 7, to the discharged position 52 illustrated in FIG. 8, the one-way valve 28 is forced open and the selected output volume of fluid flows through the one-way valve 28 and the output bore 24 into the output conduit 64 for infusion into a patient.

The cyclical or reciprocating drive 50 may be incorporated in a suitable control unit 66 such as illustrated in FIGS. 9 and 10, where the cassette 63 can be secured to the unit 66. A suitable power supply 73, such as the batteries shown, can be included in the control unit 66 for powering the drive 50.

A suitable control 70, such as a microprocessor, can be used to control operation of the pump 10, and a keyboard 72 can also be provided to allow the operator to vary the desired delivery rates, volumes, profiles and the like. Further, a suitable display 68 can be included to give the operator information regarding operation and/or malfunctions. Thus, the unit could be used to deliver a bolus dose of drugs or a substantially continuous flow of incremental small volumes of drugs or some combination thereof.

As illustrated herein, the stepped nozzle 25 and the duckbill 28 appear orientated downward. Orientating the stepped nozzle 25 and the duckbill 28 upward will help vent compressible fluids (i.e., gases) from the pump chamber 40, in some cases improving pump performance.

The infusion pump of the present invention delivers a precise output volume in response to a cyclical drive. The pump exhibits monotonicity and a high degree of linearity and granularity. The pump diaphragm is resilient yet rigid enough to prevent deformation from changes in ambient or reservoir pressure within a range of between about 7–30 psia. The inventive pump consists of only four (4) pieces, making it inexpensive and easy to manufacture. The pieces are also made of readily available materials, further minimizing pump cost. Moreover, the pump elements are compact and light weight, matting them ideal for an ambulatory pump. Because of these properties, the pump can readily be combined with a reservoir bag to form a low cost, accurate and dependable disposable cassette for use with an ambulatory pump control unit.

What is claimed is:

1. An ambulatory infusion pump for delivering a selected output volume of fluid from a fluid supply to an output conduit in response to driving by a cyclical drive, the pump comprising:
   a rigid pump housing;
   a diaphragm comprising a convex dome of spring steel in fluid tight abutment with the pump housing to define a pump chamber therebetween, the diaphragm being resiliently biased toward a selected metering position in which the diaphragm assumes a cup-shaped configuration and the pump chamber has a selected metering volume and the diaphragm further being drivable by the cyclical drive to a discharged position in which the pump chamber has a selected discharge volume which is less than the metering volume by a selected output volume, the diaphragm including integrally formed means for maintaining the output volume substantially constant notwithstanding substantial variations in fluid pressure from the fluid supply or variations in ambient pressure;
   inlet means for selectively allowing a fluid to flow between the fluid supply and the pump chamber as the diaphragm moves from the discharged position to the metering position and for stopping the fluid flow between the pump chamber and the fluid supply when the diaphragm is driven from the metering position; and
   a one-way outlet valve in fluid communication with the pump chamber permitting flow of the output volume of fluid out of the pump chamber.

2. A pump for delivering a selected output volume of fluid from a fluid supply to an output conduit in response to driving by a cyclical drive, the pump comprising:
   a rigid housing;
   a diaphragm having a peripheral edge, the peripheral edge being secured to the housing to define a pump chamber therebetween, the diaphragm otherwise being unsecured to the pump housing, the diaphragm having an inlet opening from the pump chamber to the fluid supply, the diaphragm being resiliently biased toward a metering position with the chamber having a fist selected volume, the diaphragm being drivable in response to the cyclical drive from the metering position to a discharged position having a second selected volume which is less than the first selected volume by a selected output volume;
   means for sealing the diaphragm inlet opening between the inlet opening and the cyclical driving means, the sealing means being movable between a sealing position and an unsealing position, the cyclical drive moving the sealing means to its sealing position during driving thereby closing the diaphragm inlet when the diaphragm is driven from the metering position by the cyclical drive; and
   a one-way outlet valve in fluid communication with the pump chamber permitting flow of the output volume of the fluid out of the pump chamber.

3. The pump of claim 2, wherein the diaphragm is a convex dome of spring steel with the inlet in the center of the dome, the cyclical drive engaging the center of the dome during driving.

4. The pump of claim 3 further including an arcuate shoulder on the rigid housing, the arcuate shoulder engaging the peripheral edge of the convex dome.

5. The pump of claim 2 wherein the sealing means comprises a relaxation seal resiliently biased to the unsealed position away from the diaphragm inlet, the relaxation seal being moved to the sealed position closing the diaphragm inlet in response to the cyclical drive when the cyclical drive drives the diaphragm from the metering position.

6. The pump of claim 2 further including sealing means between the diaphragm and the housing for preventing leaking of fluid therebetween.

7. A disposable ambulatory infusion pump cassette usable with a control unit having a cyclical drive to deliver a selected output volume of fluid to an output conduit for parenternal injection of the selected output volume to a patient, the cassette comprising:
   a reservoir bag defining a fluid reservoir therein for storing a fluid;
   a rigid pump housing connected to the reservoir bag;
   a diaphragm within the bag having an inlet opening, the diaphragm being in fluid tight abutment with the pump housing to define a pump chamber therebetween, the diaphragm being resiliently biased toward a cup-shaped metering position with the pump chamber having a selected metering volume, said diaphragm further being drivable by the cyclical drive to a discharged position in which the pump chamber has a selected discharged volume which is less than the metering volume by a selected output volume;
   means for closing the diaphragm inlet when the diaphragm is driven from the metering position by the cyclical drive; and
   a one-way outlet valve permitting flow of the output volume of the fluid from the pump chamber.

8. The cassette of claim 7 further including a seal between the pump and the diaphragm for providing a fluid tight seal therebetween.

9. The cassette of claim 7 wherein the diaphragm is a convex dome of spring steel with the inlet in the center of the convex dome, the cyclical driven engaging the center of the convex dome when the convex dome is driven from the metering position.

10. The cassette of claim 7, wherein the closing means comprises a relaxation seal resiliently biased from the diaphragm inlet, the relaxation seal closing the diaphragm inlet in response to the cyclical drive when driving the diaphragm from the metering position.

11. The cassette of claim 7, wherein the closing means comprises a cup-shaped relaxation seal with its top disposed over and resiliently biased from the diaphragm inlet, the relaxation seal having a plurality of perforations therein for the flow of fluid therethrough.

12. A pump for delivering a selected output volume of fluid from a fluid supply to an output conduit in response to driving by a cyclical drive, the pump comprising:

a rigid pump housing;
a diaphragm in fluid tight abutment with the pump housing to define a pump chamber therebetween, the diaphragm being resiliently biased toward a selected metering position in which the diaphragm assumes a cup-shaped configuration and the pump chamber has a selected metering volume and the diaphragm further being drivable by the cyclical drive to a discharged position in which the pump chamber has a selected discharged volume which is less than the metering volume by a selected output volume;
inlet means for selectively allowing a fluid to flow between the fluid supply and the pump chamber as the diaphragm moves from the discharged position to the metering position and for stopping the fluid flow between the pump chamber and the fluid supply when the diaphragm is driven from the metering position, comprising, an inlet hole in the diaphragm, a relaxation seal and means resiliently biasing the relaxation seal away from the inlet hole, the relaxation seal closing the inlet hole in response to the cyclical drive driving the diaphragm from the metering position; and
a one-way outlet valve in fluid communication with the pump chamber permitting flow of the output volume of fluid out of the pump chamber.

13. The pump of claim 12 wherein the biasing means is integrally formed with the relaxation seal, the biasing means including a plurality of perforations for the flow of fluid therethrough, the biasing means and relaxation seal being disposed over the diaphragm.

14. The pump of claim 12 wherein the diaphragm is a convex dome of spring steel.

15. A pump for delivering a selected output volume of fluid from a fluid supply to an output conduit in response to driving by a cyclical drive, the pump comprising:

a rigid pump housing;
a diaphragm in fluid fight abutment with the pump housing to define a pump chamber therebetween, the diaphragm having an opening for fluid communication between a fluid supply and the pump chamber, the diaphragm being resiliently biased toward a selected metering position in which the diaphragm assumes a cup-shaped configuration and the pump chamber has a selected metering volume and the diaphragm further being drivable by the cyclical drive to a discharged position in which the pump chamber has a selected discharged volume which is less than the metering volume by a selected output volume;
valve means for selectively allowing a fluid to flow between the fluid supply and the pump chamber through the opening as the diaphragm moves from the discharged position to the metering position and for stopping the fluid flow between the pump chamber and the fluid supply when the diaphragm is driven from the metering position; and
a one-way outlet valve in fluid communication with the pump chamber permitting flow of the output volume of fluid out of the pump chamber.

16. The pump of claim 15 wherein the valve means comprises:
a relaxation seal; and
means resiliently biasing the relaxation seal away from the opening, the relaxation seal closing the opening in response to the cyclical driven driving the diaphragm from the metering position.

17. The pump of claim 16 wherein the biasing means is integrally formed with the relaxation seal, the biasing means including a plurality of perforations for the flow of fluid therethrough, the biasing means and relaxation seal being disposed over the diaphragm.

18. The pump of claim 15 wherein the diaphragm is a convex dome of spring steel.

19. The pump of claim 18 wherein the opening is in the center of the convex dome and the valve means comprises:
a relaxation seal; and
means resiliently biasing the relaxation seal away from the opening, the relaxation seal closing the opening in response to the cyclical driven driving the diaphragm from the metering position.

20. A pump for delivering a selected output volume of fluid from a fluid supply to an output conduit in response to driving by a cyclical drive, the pump comprising:

a rigid pump housing;
a diaphragm in fluid tight abutment with the pump housing to define a pump chamber therebetween, the diaphragm including integral means resiliently biasing the diaphragm toward a selected metering position in which the diaphragm has its lowest potential energy and the pump chamber has a selected metering volume and the diaphragm further being drivable by a cyclical drive to a discharged position in which the diaphragm has less potential energy than it does in any other position except the metering position and in which the pump chamber has a selected discharged volume which is less than the metering volume by a selected output volume;
inlet means for selectively allowing a fluid to flow between the fluid supply and the pump chamber as the diaphragm moves from the discharged position to the metering position and for stopping the fluid flow between the pump chamber and the fluid supply when the diaphragm is driven from the metering position, the inlet means comprising an inlet hole in the diaphragm, a relaxation seal, and means resiliently biasing the relaxation seal away from the inlet hole, the relaxation seal closing the inlet hole in response to the cyclical driving means driving the diaphragm from the metering position; and a one-way outlet valve in fluid communication with the pump chamber permitting flow of the output volume of fluid out of the pump chamber.

21. The pump of claim 20 wherein the biasing means is integrally formed with the relaxation seal, the biasing means including a plurality of perforations for the flow of fluid therethrough, the biasing means and relaxation seal being disposed over the diaphragm.

22. The pump of claim 20 wherein the diaphragm is a convex dome of spring steel.

* * * * *